(12) United States Patent
Reneker et al.

(10) Patent No.: US 8,367,570 B2
(45) Date of Patent: Feb. 5, 2013

(54) MECHANICALLY STRONG ABSORBENT NON-WOVEN FIBROUS MATS

(75) Inventors: Darrell H. Reneker, Akron, OH (US); Daniel J. Smith, Stow, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 11/435,066

(22) Filed: May 16, 2006

(65) Prior Publication Data

US 2006/0246798 A1 Nov. 2, 2006

Related U.S. Application Data

(63) Continuation-in-part of application No. 10/510,457, filed as application No. PCT/US03/10652 on Apr. 4, 2003, now Pat. No. 7,765,647.

(60) Provisional application No. 60/681,544, filed on May 16, 2005, provisional application No. 60/370,051, filed on Apr. 4, 2002.

(51) Int. Cl.
*D04H 1/00* (2006.01)

(52) U.S. Cl. ........ 442/327; 442/329; 442/340; 442/375; 442/381; 442/387

(58) Field of Classification Search ................ 442/327, 442/329, 340, 375, 381, 387
See application file for complete search history.

(56) References Cited

U.S. PATENT DOCUMENTS

| | | | |
|---|---|---|---|
| 3,916,900 A | 11/1975 | Breyer et al. | |
| 4,043,331 A | 8/1977 | Martin et al. | |
| 4,685,907 A * | 8/1987 | Agren et al. | 424/447 |
| 4,699,133 A | 10/1987 | Schafer et al. | |
| 4,707,398 A * | 11/1987 | Boggs | 442/329 |
| 4,814,131 A | 3/1989 | Atlas | |
| 5,102,601 A | 4/1992 | Farris et al. | |
| 5,238,733 A | 8/1993 | Joseph et al. | |
| 5,342,686 A | 8/1994 | Guersen et al. | |
| 5,356,403 A | 10/1994 | Faulks et al. | |
| 5,601,542 A | 2/1997 | Melius et al. | |
| 5,683,794 A | 11/1997 | Wadsworth et al. | |
| 5,711,960 A | 1/1998 | Shikinami | |
| 5,795,584 A | 8/1998 | Totakura et al. | |
| 5,935,370 A | 8/1999 | Weimer et al. | |
| 6,033,684 A | 3/2000 | Norcia | |
| 6,040,088 A | 3/2000 | Bennett et al. | |
| 6,114,024 A | 9/2000 | Forte | |
| 6,124,058 A | 9/2000 | Ohmory et al. | |

(Continued)

FOREIGN PATENT DOCUMENTS

EP 0361842 A2 4/1990
EP 1059908 10/2004

(Continued)

OTHER PUBLICATIONS

Hansen, L., Water Absorption and Mechanical Properties of Electrospun Structured Hydrogels, Applied Polymer Science, 2005.

(Continued)

*Primary Examiner* — Peter Y Choi
(74) *Attorney, Agent, or Firm* — Renner Kenner; Greive Bobak; Taylor Weber

(57) ABSTRACT

The present invention is generally directed to a liquid entrapping device having the capacity to absorb liquids. More particularly, the present invention is directed to a liquid entrapping device comprising an absorbent component, hydrophilic elastomeric fibrous component in fluid communication therewith, and optionally an adhesive component. The present invention is also directed to a liquid entrapping device having the capacity to absorb liquids while maintaining a suitable degree of mechanical strength. Furthermore, the present invention is generally directed to methods for making and using the foregoing devices and materials.

43 Claims, 10 Drawing Sheets

U.S. PATENT DOCUMENTS

| | | |
|---|---|---|
| 6,198,016 B1 * | 3/2001 | Lucast et al. ............... 602/41 |
| 6,252,129 B1 | 6/2001 | Coffee |
| 6,265,333 B1 | 7/2001 | Dzenis et al. |
| 6,270,794 B1 * | 8/2001 | Cilento et al. ............ 424/445 |
| 6,287,679 B1 | 9/2001 | Pappas et al. |
| 6,306,424 B1 | 10/2001 | Vyakarnam et al. |
| 6,368,687 B1 * | 4/2002 | Joseph et al. ............ 428/40.1 |
| 6,573,419 B2 | 6/2003 | Naimer |
| 6,750,262 B1 | 6/2004 | Hahnle et al. |
| 6,753,454 B1 | 6/2004 | Smith et al. |
| 6,824,534 B2 | 11/2004 | Mishima et al. |
| 2002/0017354 A1 * | 2/2002 | Riddell ..................... 156/62.4 |
| 2002/0151634 A1 * | 10/2002 | Rohrbaugh et al. ........ 524/430 |
| 2004/0265387 A1 | 12/2004 | Hermeling et al. |
| 2005/0004541 A1 | 1/2005 | Roberts |
| 2005/0008776 A1 | 1/2005 | Chhabra et al. |

FOREIGN PATENT DOCUMENTS

| | | |
|---|---|---|
| WO | WO 93/07321 A1 | 4/1993 |
| WO | WO 97/39170 A1 | 10/1997 |
| WO | WO 98/03267 A1 | 1/1998 |
| WO | WO 98/35631 A1 | 8/1998 |
| WO | WO 01/23653 A1 | 4/2001 |
| WO | WO 01/27365 A1 | 4/2001 |
| WO | WO 01/54667 A1 | 8/2001 |
| WO | WO 0215816 A2 * | 2/2002 |
| WO | WO 03/086234 | 10/2003 |
| WO | WO 2004/049993 | 6/2004 |
| WO | WO 2005/016205 | 2/2005 |

OTHER PUBLICATIONS

European Search Report Dated May 6, 2006 for European Patent Application No. 03726214.4-2107 from related U.S. Appl. No. 10/510,457.

Office Action Dated Apr. 15, 2009 for European Patent Application No. 03726214.4-2107 from related U.S. Appl. No. 10/510,457.

Office Action Dated Nov. 29, 2006 for European Patent Application No. 03726214.4-2107 from related U.S. Appl. No. 10/510,457.

* cited by examiner

Dumbell Type 5-D638

MECHANICALLY STRONG ABSORBENT NON-WOVEN FIBROUS MATS

RELATED APPLICATION DATA

This application is both (1) a continuation of U.S. Provisional Application No. 60/681,544 filed May 16, 2005; and (2) a continuation-in-part of Ser. No. 10/510,457 filed Jul. 25, 2005 now U.S. Pat. No. 7,765,647; which is a national phase application of PCT/US03/10652 filed Apr. 4, 2003; which claims priority to U.S. Provisional Application No. 60/370,051 filed Apr. 4, 2002; each of which are hereby incorporated herein by reference in their entireties.

BACKGROUND OF THE INVENTION

The present invention relates to mechanically strong absorbent materials. More particularly such materials comprise at least one hydrophilic elastomeric fibrous component (HEFC) and at least one absorbent component. Additionally, some embodiments can further comprise an adhesive component. The HEFC can comprise a block copolymer wherein the blocks comprise an elastomeric block and a hydrophilic block. Alternatively, the HEFC can comprise a mixture or solid solution of hydrophilic polymer and elastomeric polymer. The absorbent component is generally in physical proximity to the HEFC resulting in fluid communication therewith. In general, the system operates in the following manner: the HEFC absorbs a liquid and transfers it to the absorbent component where the fluid remains entrapped and/or bound. Embodiments that also include an adhesive component can be fixed in place at a locus where liquid is to be absorbed.

A variety of methods are known in the textile field for creating fibers compatible with the present invention. Melt-blowing, nanofibers-by-gas-jet (NGJ), and electrospinning are non-limiting examples of these techniques. In a melt-blowing process, a stream of molten polymer or other fiber-forming material is typically extruded into a jet of gas to form fibers. The resulting fibers are typically greater than 1,000 nanometers in diameter, and more typically, greater than 10,000 nanometers in diameter. A technique and apparatus for forming fibers having a diameter of less than 3,000 nanometers according to the NGJ technique is described in U.S. Pat. Nos. 6,382,526 and 6,520,425, and these patents are hereby incorporated by reference in their entireties. Here, as well as throughout this application, when an inconsistency exists between the present application and documents incorporated by reference the present application controls.

The electrospinning, (i.e. electrostatic spinning), of liquids and/or solutions capable of forming fibers is well known in the art. Electrospinning has been described in a number of patents as well as in scientific literature. The process of electrospinning generally involves creating an electric field at the surface of a liquid. The resulting electrical forces create a jet of liquid that carries an electric charge. Thus, the liquid jets can be attracted to other electrically charged objects having a suitable electrical potential. As the jet of liquid elongates and travels, the fiber-forming material within the liquid jet dries and hardens. Hardening and drying of the elongated liquid jet can be caused by a variety of means including, without limitation, cooling the liquid; solvent evaporation (i.e. physically induced hardening); or by a curing mechanism (i.e. chemically induced hardening). The resulting charged fibers are collected on a suitably located, oppositely charged receiver and subsequently removed from it as needed, or directly applied to an oppositely charged or grounded generalized target area.

Fibers produced by this process have been used in a wide variety of applications, and are known, from U.S. Pat. No. 4,043,331 to be particularly useful in forming non-woven mats suitable for use in wound dressings. One of the major advantages of using electrospun fibers in wound dressings, is that very thin fibers can be produced having diameters, usually on the order of about 50 nanometers to about 25 microns, and more advantageously, on the order of about 50 nanometers to about 5 microns. These fibers can be collected and formed into non-woven mats of any desired shape and thickness. It will be appreciated that a mat with very small interstices and high surface area per unit mass can be produced because of the very small diameter of the fibers.

Medical dressings formed using non-woven mats of these polymeric fibers can provide particular benefits that depend upon the type of polymer or polymers used, as disclosed by U.S. Pat. No. 4,043,331. A water-wettable or hydrophilic polymer, e.g. a polyurethane, can be used. Alternatively, a polymer that is not water-wettable, or that is at least weakly hydrophobic, e.g. a saturated polyester, can be employed. Where the dressing is formed from a wettable polymer, blood or serum escaping from the wound tends to penetrate the dressing and the high surface area encourages clotting. Such dressings can be used as emergency dressings to halt bleeding. On the other hand, where the dressing is formed from a non-wetting polymer, and where the interstices between the fibers are sufficiently small, i.e., on the order of less than about 100 nanometers, tissue fluids, including blood, tend not to permeate the dressing. Consequently, the fluids are retained adjacent to the wound where clotting will occur. Subsequent removal of such a dressing is facilitated by the absence of blood clots permeating the dressing material. Still further, U.S. Pat. No. 4,043,331 suggests that such dressings have the advantage that they are usually sufficiently porous to allow interchange of oxygen and water vapor between the atmosphere and the surface of the wound.

Besides providing variability as to the diameter of the fibers or the shape, thickness, or porosity of any non-woven mat produced therefrom, the ability to electrospin the fibers also allows for controlled variations in the composition of the fibers, their density of deposition and their inherent strength. The above-identified U.S. patent indicates that it is also possible to post-treat the non-woven mats with other materials to modify their properties. For example, one could increase the strength of the mat using an appropriate binder or increase water resistance by post-treating the mat with silicone or other water-resistant material, such as perfluoro alkyl methacrylate. Alternatively, strength can be increased by utilizing fibers of polytetrafluoroethylene (PTFE).

By varying the composition of the fibers being formed, fibers having different physical or chemical properties can be obtained. This can be accomplished either by spinning a liquid containing a plurality of components, each of which can contribute a desired characteristic to the finished product, or by simultaneously spinning, from multiple liquid sources, fibers of different compositions that are then simultaneously deposited to form a mat. It is also known in the prior art that molecules, particles, and droplets can be incorporated into electrospun nanofibers during the electrospinning process. The resulting mat, of course, would consist of intimately intermingled fibers of different materials.

Ordinarily, wetting the fibrous article compromises strength. This is especially problematic in applications such as diapers, tampons, and the like inasmuch as these applications require both strength and absorbency. Existing patents and printed publications disclose various solutions to this absorption problem, but each is distinguishable from the present invention as will become clear herein.

For instance, one option available in the art is to produce a mat having a plurality of fibrous layers of different materials. For example, wettable and non-wettable polymers offer differing properties. Wettable polymers tend to be highly absorbent but provide mats that are relatively weak, while non-wetting polymers tend to be non-absorbent but provide relatively strong mats. The wettable polymer layer or layers contribute a relatively high level of absorbency to the article while the non-wetting polymer layer or layers contribute a relatively high level of strength. Use of such layering structures, suffers from the disadvantage that the hydrophobic layer can form a barrier to liquids and interfere with the absorption of liquid by the wettable layer. Additionally, upon absorption of liquid, the wettable polymer layer will weaken and misalignment, slipping, or even separation of the layers can occur, possibly resulting in structural failure of the article.

U.S. Pat. No. 4,043,331 suggests that strong, non-woven mats comprising a plurality of fibers of organic, namely polymeric, material can be produced by electrostatically spinning the fibers from a liquid consisting of the material or its precursor. These fibers are collected on a suitably charged receiver. The mats or linings formed on the receiver can then be transferred and used alone or in conjunction with other previously constructed components such as, for example, mats of woven fibers and backing layers to provide a wound dressing having desired characteristics. For instance, in producing wound dressings, additional supports or reinforcement such as mats or linings of fibers, or backing layers can be required in order to adhere the wound dressing to the skin and to provide other desirable properties to the wound dressing. As an example, a mat or lining of non-woven fibers can contain materials having antiseptic or wound-healing properties. Surface treatments of the already formed non-woven mats can also provide added benefits in the production of such wound dressings. However, U.S. Pat. No. 4,043,331 does not provide a medical dressing that adheres to undamaged skin only. It also does not provide a single-component dressing that can adhere to a desired area of a patient, or a dressing comprised of composite fibers that vary in their composition along their length.

It has also been described in PCT International Publication No. WO98/03267 to electrostatically spin a wound dressing in place over a wound. In such a use, the body itself is grounded and acts as a collector of the electrospun fibers. This method of synthesizing a wound dressing allows for solution of some of the problems associated with bandage and gauze storage and preparation. It is well known for example, that gauze and bandages must be stored and maintained in a sterile environment in order to offer the greatest protection in healing wounds. If the gauze or bandages are not sterile, these products offer little help in protecting the wound. Electrospinning a wound dressing in place, over a wound, from a sterile liquid, eliminates these problems.

International Publication No. WO 01/27365, the disclosure of which is incorporated herein by reference in its entirety, describes an electrospun fiber containing a substantially homogeneous mixture of a hydrophilic polymer, a polymer that is at least weakly hydrophobic, and optionally, a pH adjusting compound. The fibers can be deposited directly on their intended usage area without first applying the fibers to a transient, charged receiver or subjecting it to other intermediate fabrication steps. The resulting fibers, however, do not provide a dressing that adheres only to undamaged skin.

International patent application WO 2005/016205 provides an absorbent core made from a matrix of fibers wherein the matrix is reinforced with a stretchable reinforcing member such as scrim, wherein the fibers are anchored to the reinforcing member. This differs from the present invention in part because the reinforcing member and fiber matrix are wholly separate components. In contrast, the present invention is self-reinforcing in the sense that it incorporates hydrophilic character and elastomeric character in a single fibrous mat. The strength of the fibrous mat of the present invention does not depend on anchoring to a separate body such as a scrim. Moreover, the '205 publication does not disclose the use of an absorbent component separate from the fibrous component as does the present invention.

Thus, there is a need in the art for an absorbent, liquid-entrapping, device comprising a hydrophilic elastomeric fibrous component in physical proximity to an absorbent component resulting in fluid communication therewith. Furthermore, there is a need for such an arrangement wherein one or more liquids enter the fibrous component, which transmits the liquids to the absorbent component thereby entrapping the liquids.

BRIEF SUMMARY OF THE INVENTION

The present invention generally relates to absorbent materials that remain mechanically strong when wet. More particularly such materials comprise at least one hydrophilic elastomeric fibrous component (HEFC) and at least one absorbent component. In some embodiments, the present invention can further comprise an adhesive component. The HEFC can comprise a block copolymer wherein the blocks comprise an elastomeric block and a hydrophilic block. In still other embodiments, the HEFC can comprise a mixture or solid solution of hydrophilic polymer and elastomeric polymer. The absorbent component is generally in physical proximity to the HEFC resulting in fluid communication therewith. The combination of the HEFC and absorbent component can be arranged into a woven or non-woven mat, or any other appropriate form. An adhesive component can be disposed on one or more surfaces of the mat thereby enabling it to be affixed to an object, for instance, to a patient's wound.

In one embodiment the present invention relates to a liquid entrapping device comprising: an absorbent component; and a hydrophilic elastomeric fibrous component, wherein the absorbent component and the hydrophilic elastomeric fibrous component are in physical proximity thereby resulting in fluid communication, and wherein the absorbent component is more absorbent than the hydrophilic elastomeric fibrous component.

In another embodiment the present invention relates to a process for making a liquid entrapping device comprising: spinning at least one fiber from a solution comprising a hydrophilogenic elastomerogenic component and an absorbent component, wherein the fiber includes an absorbent component in physical proximity to the hydrophilogenic elastomerogenic component, thereby resulting in fluid communication therewith.

In another embodiment the present invention relates to a process for using a liquid entrapping device comprising the steps of placing a liquid entrapping device in contact with at least one liquid.

In another embodiment the present invention relates to a means for absorbing liquids comprising a fluid conductive means; and an absorbent means, wherein the means for absorbing remains resistant to tensile stress after absorbing one or more liquids.

In another embodiment the present invention also relates to a non-woven fiber assembly comprising one or more fibers wherein the fibers comprise: an adhesive component; an elastomeric; and a hydrophilic component.

In still another embodiment the present invention relates to a method of making a non-woven fiber assembly, the method comprising: providing at least one fiber-forming material; and forming at least one fiber from the at least one fiber-forming material, wherein the at least one fiber forming material comprises an adhesive component, an elastomeric component, and a hydrophilic component.

In still another embodiment the present invention relates to a method of treating a patient comprising: applying a non-woven fiber assembly to a predetermined area of the patient, wherein the non-woven fiber assembly contains one or more fibers comprising an adhesive component, an elastomeric component, and a hydrophilic component.

In still yet another embodiment the present invention relates to an apparatus for forming at least one composite fiber, the fiber comprising a hydrophilic component, an elastomeric component and an adhesive component, wherein the apparatus comprises: a plurality of reservoirs for containing a plurality of fiber-forming materials; a plurality of valves, each independently in communication with a reservoir; and a fiber-forming device selected from a spinnerette, a NGJ nozzle, and an electrospinning device, in communication with the valves.

DETAILED DESCRIPTION OF THE INVENTION

Figure 1:
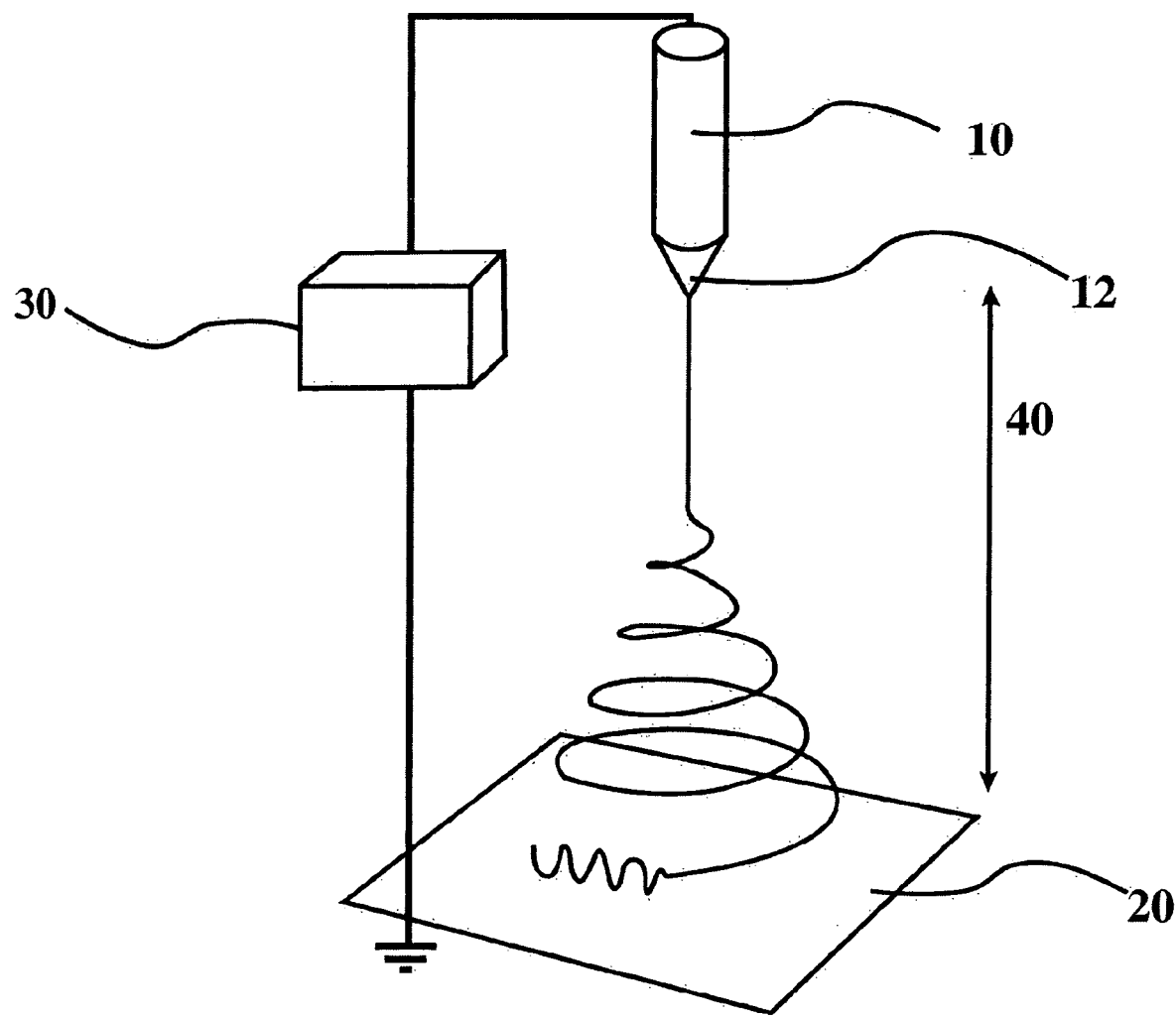
FIG. 1 is a schematic representation of an apparatus for forming composite fibers according to the present invention.

The present invention generally relates to absorbent materials that remain mechanically strong when wet. More particularly such materials comprise at least one hydrophilic elastomeric fibrous component (HEFC) and at least one absorbent component. In some embodiments, the present invention can further comprise an adhesive component. The HEFC can comprise a block copolymer wherein the blocks comprise an elastomeric block and a hydrophilic block. Alternatively, the HEFC can comprise a mixture or solid solution of hydrophilic polymer and elastomeric polymer. The absorbent component is generally in physical proximity to the HEFC resulting in fluid communication therewith. The combination of the HEFC and absorbent component can be arranged into a woven or non-woven mat, or any other appropriate form.

In one embodiment, the HEFC of the present invention functions as a conduit for delivering liquids to an absorbent component where the liquid will be entrapped. Thus, the HEFC acts in the manner of a wick in the sense that it provides a means for fluid flow. This wicking property coupled with a difference in absorption capacity and rate between the HEFC and the absorbent component results in a net fluid flow to the absorbent component. That is to say, that since the HEFC both absorbs more quickly than the absorbent component and has a smaller holding capacity it tends to reach its holding capacity more quickly. Thus, there tends to be a net fluid flow from the fiber to the absorbent component.

In general, the present invention operates in the following manner. A fibrous mat comprising the HEFC and absorbent component is placed in fluid communication with a liquid to be absorbed. The HEFC absorbs a liquid and transfers it to the absorbent component where the fluid remains entrapped. The elastomeric property of the fibrous component serves to accommodate the expansion of the absorbent component without resulting in rupture of the fibrous component. In accordance with the present invention, the fibrous component stretches in order to tolerate the dimensional changes that result from the absorbent component taking up liquids. Additionally, some embodiments can include an adhesive component for affixing the fibrous mat to an object from which one or more liquids are to be absorbed.

As used herein, the term absorbent includes compounds/substances capable of being wetted with a liquid. As used herein, the term elastomer includes any polymeric material that is capable of elastically deforming under a load and substantially resuming its original shape when the load is removed. As used herein, the term hydrophilic includes being capable of absorbing aqueous or otherwise polar liquids. Materials can be an elastomer, hydrophilic and an absorbent simultaneously. As used herein the term super-absorbent includes any material capable of absorbing about 50 times its own weight in liquid or more. Super-absorbents can be, without limitation, organic polymers and porous clays. As used herein, the term "absorbency" refers to the mass of liquid retained per mass of absorbent device including both structural and absorbent components. Generally, the absorbencies referred to herein are equilibrium values. As used herein, the noun form of the term "absorption" comprises the amount of liquid absorbed. As used herein, "fiber assembly" includes at least one fiber in fluid communication with at least one absorbent component.

As used herein, elastomerogenic refers to the capacity of a compound to form an elastomer. Similarly, as used herein, hydrophilogenic refers to the capacity of a compound to form a hydrophilic polymer. Although the terms elastomerogenic and hydrophilogenic describe the elastomeric and hydrophilic properties of materials downstream from themselves, elastomerogenic and hydrophilogenic materials also can be hydrophilic and/or elastomeric. For instance, a hydrophilogenic material can itself be hydrophilic; however, a hydrophilogenic material is not required to be hydrophilic. The same holds true for elastomerogenic materials.

Hydrophilic elastomeric fibrous component as used herein refers to a liquid-wicking member having the capacity to absorb liquids and serve as a conduit for delivering such liquids to another material. The word order of the term "HEFC" has no significance. Particularly, it provides no indication as to whether the material is predominantly hydrophilic or predominantly elastomeric. For example, the phrase elastomeric hydrophilic fibrous component is equivalent to hydrophilic elastomeric fibrous component. The same is true for every other permutation of the word order. Likewise, the term hydrophilogenic elastomerogenic component is equivalent to elastomerogenic hydrophilogenic component.

The HEFC can comprise any hydrophilic elastomeric material provided it is capable of: (1) being spun into fibers, and (2) absorbing and wicking liquids. Advantageously, such a material is also capable of withstanding the strain that results from dimensional changes of the absorbent component. Materials within the scope of the present invention can be blends, mixtures or solid solutions of elastomerogenic and hydrophilogenic subcomponents. Alternatively, such materials can be copolymers of elastomeric mers and hydrophilic mers, e.g. random copolymers, block copolymers, and the like. In another embodiment, the present invention can also include a copolymer comprising adhesive component(s) in addition to elastomeric and hydrophilic components.

Still further materials within the scope of the present invention for forming the HEFC include homopolymers wherein the components thereof are both hydrophilic and elastomeric. Specific materials within the scope of the present invention include, without limitation, zein protein, polyester elastomers, polydimethylsiloxane, hydrophilic poly(ether-co-ester) elastomers, silicone-co-polyethyleneglycol elastomers, polyacrylates, thermoplastic polyurethanes, poly(ether-co-urethanes), and polyurethanes. Particularly advantageous materials include, without limitation, poly(ether-co-urethanes), and polyurethanes.

Any absorbent material can be used as the absorbent component of the present invention provided it is capable of being in physical proximity to the HEFC resulting in fluid communication therewith. Generally, this means that the material must be wettable by an aqueous or otherwise polar liquid. More particularly, materials within the scope of the present invention advantageously have a greater liquid holding capacity per unit mass than the HEFC. In contrast to the HEFC, no particular morphology is necessary to the operation of the absorbent component. For example, the absorbent component can be, without limitation, irregular, amorphous, globular, elongated, fibrous, azimuthal, ellipsoidal, or spherical. Moreover, no particular stress-strain relationship is necessary to the performance of the absorbent material. Thus, the absorbent material can be, without limitation, substantially rigid, pliable, elastic, gelatinous, fluid or brittle. Absorbent materials include, without limitation, polyesters, polyethers, polyester-polyethers, polymers having pendant acids or pendant hydroxyls, polysiloxanes, polyacrylamides, kaolins, serpentines, smectites, glauconite, chlorites, vermiculites, attapulgite, sepiolite, allophane and imogolite, sodium polyacrylates, and 2-propenamide-co-2-propenoic acid. Particularly advantageous materials include, without limitation, sodium polyacrylates, and 2-propenamide-co-2-propenoic acid.

The absorbent material can have any of a variety of absorbencies; however, advantageously the absorbent material has a greater absorbency than the HEFC. More advantageously, the absorbent material is a super-absorbent.

The absorbent component can be distributed in any manner provided it is in physical proximity to the HEFC, resulting in fluid communication therewith. For instance, the absorbent material can be coated on the surface of the HEFC. More specifically, it can be physisorbed or chemisorbed to the surface of the HEFC, or it can be affixed to the surface in any other appropriate manner. In another example, the absorbent material can be mechanically entrapped or entangled in the hydrophilic elastomeric fibers. Alternatively, the absorbent component can be embedded in the HEFC. Additionally, any combination of the foregoing arrangements is also within the scope of the present invention.

Any of the foregoing distributions can be advantageous depending upon the physical properties of the absorbent component. For instance, if the absorbent component has a tendency to slough off it can be advantageous to embed it in the HEFC rather than affix it to the fiber surface. On the other hand, if the absorbent material can be securely affixed to the outer surface of the hydrophilic elastomeric fibers then the fibers can be coated with the absorbent rather than embedding it in the fibers. Additionally, if the mass transfer rate from the fiber to the absorbent material is slow so that absorption is unacceptably hindered, then coating the absorbent component onto the fibers can be advantageous over embedding. Additionally, one or more of any of the foregoing arrangements can be used in any combination thereof.

In one embodiment a solution of a hydrophilic material is mixed with a solution of an elastomeric material and the mixture of the two is then spun resulting in a fiber comprising both materials. Fibers made in this manner can have a homogenous composition, wherein the elastomeric and hydrophilic materials are uniformly distributed. Alternatively, the fibers can comprise well-defined phases, or a portion of the fiber can be a homogenous solid solution and a portion can be phase-separated. In another embodiment, the fiber can comprise a block copolymer wherein the blocks further comprise elastomeric blocks and hydrophilic blocks. The blocks can be arranged randomly or in any of a variety of suitable patterns.

As mentioned above, an embodiment of the present invention can provide a non-woven fiber assembly comprising at least one fiber and containing an optional adhesive component, an elastomeric component, and a hydrophilic component. The at least one fiber can contain a series of segments such as a segment that is primarily or even totally an adhesive component, a segment that is primarily or totally an elastomeric component, and a segment that is primarily or totally a hydrophilic component. When the at least one fiber has such an arrangement of components, the different segments can be arranged in any of a number of orders, depending on the needs of a particular application. It is envisioned that a particularly useful arrangement would include a segment that is at least primarily an adhesive component located adjacent to a segment that is at least primarily a hydrophilic component, which is, in turn, located adjacent to segment that is at least primarily an elastomeric component. The composite fiber can also include two or more components in a segment of fiber. The composition of each segment and number of segments can also vary over the length of the fiber. Additionally, the transition between segments can be either smooth or abrupt. Alternatively, the composition of the fiber can be constant over its length. The non woven fiber assembly can also comprise a plurality of fibers wherein different fibers, individually or in combination, supply each component.

Methods of making a non-woven fiber assembly, according to embodiments of the present invention that contain an adhesive component, include the following. Forming at least one fiber, the at least one fiber containing an adhesive component, an elastomeric component, and a hydrophilic component. The at least one fiber can be formed by any technique that is compatible with each of the components of the fiber or fibers. It is envisioned that melt-blowing, the NGJ technique, and electrospinning are suitable methods for forming fibers according to adhesive-containing embodiments of the present to invention. Electrospinning provides particular advantages. Fibers can also be formed by other techniques, including phase separation, casting in pores, and slitting of a film.

When fibers having very small diameters are formed, a fibrous mat with very small interstices and high surface area is produced. Non-woven fiber assemblies according to the present invention are useful in, but not limited to, medical dressings, diapers, feminine hygiene products, absorbent towels or wipes for the skin, and transdermal or oral delivery systems for therapeutic and prophylactic substances. It is also envisioned that the non-woven fiber assemblies can also be used for other purposes such as spill management, water transport and management in fuel cells, and for collecting and transporting water or other fluids from coalescence filters.

When the non-woven fiber assembly forms a medical dressing, the resultant medical dressing is microporous and breathable, but is resistant to high airflow. These are important and desirable characteristics of medical dressings. Generally, pores sizes for the medical dressing produced using such techniques range from about 50 nm to about 1000 nm, or 100 nm to 750 nm, or 250 nm to 500 nm, or even 300 to 400 nm. Here, as everywhere in the specification, ranges can be combined. In some embodiments, the pores of the present invention are small enough to protect the wound from bacterial penetration via aerosol particle capture mechanisms. Furthermore, in some embodiments such pores can also hinder the passage of viral particles through the dressing to the wound.

The non-woven mats or fibrous mats of the present invention advantageously have high surface areas of at least about 5 $m^2/g$, and more advantageously, about 100 $m^2/g$ for efficient fluid absorption and dermal delivery. The high surface areas can also impart high hemostatic potential to the dressing.

When used as a medical dressing, the non-woven fiber assembly of the present invention provides greater water vapor permeability, as expressed by water vapor flux, than commercial barrier film dressings. In one embodiment, the electrospun fibrous mat forms a medical dressing that has a water vapor flux at least about ten fold greater than that of solid film barrier dressings. Advantageously, the medical dressing provides at least about a 30-fold greater water vapor flux than a commercial barrier film. More advantageously, the medical dressing provides at least about a 30-fold greater water vapor flux than a commercial barrier film.

The appropriate thickness of the fibers of the dressing depends on factors such as the fiber-forming materials used, the diameter of the fibers, the structural arrangement of the fibers, the size of the pores formed by the fibers as well as the desired degree of air permeability and protection from contaminants. For example, the fibers can form a medical dressing when applied at a coating level of as little as about 0.1 $g/m^2$. The fibers can also be applied at a coating level of between about 0.1 and about 100 $g/m^2$. At one thickness, the fibers of the medical dressing provide greater than 97 percent filtration efficiency against aerosols between about 0.5 μm and about 20 μm in diameter. At another thickness, the fibers provide greater than 97 percent filtration efficiency against aerosols between about 0.1 μm and about 20 μm in diameter. The fibers can also be applied at a thickness that provides for substantially complete filtration of aerosols between about 0.5 and about 20 μm in diameter or even about 0.1 μm to about 20 μm in diameter.

While the medical dressing provides an effective barrier to contamination, it also allows the passage of air. This permits oxygen to penetrate the dressing and contact a wound, burn, or other protected area, thereby permitting accelerated healing and a decreased likelihood of infection compared to wound dressings that do not permit airflow to the protected area. In one example, the medical dressing provides an airflow resistance of less than about $5 \times 10^9$ $m^{-1}$. Advantageously, the medical dressing has an airflow resistance of less than about $2 \times 10^8$ $m^{-1}$. In another example, the medical dressing has an airflow resistance of less than about $2 \times 10^7$ $m^{-1}$.

The fibers and the resultant medical dressings and other non-woven fiber assemblies of the present invention are lightweight, oxygen and moisture permeable, yet protect against airborne contaminants such as dust, microbes, and/or other infectious agents. The ability of the fibrous mat fibers to transport and deliver therapeutic additives to the to site of a wound is also important. This ability to transport and deliver additives can be controlled through the choice of polymer carrier, density and thickness of the non-woven sheet of fibers, and/or layering of different fibrous mat fiber compositions.

With respect to the fibers used in a medical dressing, it will be understood that the fibers can be dry, and form strong fibrous mats. However, in some instances, a wet fiber can be employed. Although wet fibers can be strong, wet fibers are generally softer and conform to the surface of the substrate to which they are applied better than dry fibers. Other advantages can include those set forth previously in the discussion above related to U.S. Pat. No. 4,043,331. In any event, the ability to form the fibers of the present invention directly onto the surface of a wound allows for improved flexibility in the composition of the fibers, improved porosity of the fibrous mat, and improved strength, all in an inexpensive and timely manner. Moreover, by directly applying the fibers to a wound the fibers can be advantageously placed in intimate and shape-forming contact with the total wound surface even if the healthy tissue is deep within the wound. This enables efficient removal of dead cells, fluid or bacteria from deep within the wound when the dressing is changed, thereby reducing or eliminating the need for debridement of the wound. Direct contact with the surface of the wound will also enable improved drug delivery to the wound. Finally, it will be appreciated that direct application provides for improved and, in fact, inherent, sterility of the fibers and, therefore, the dressing, thereby eliminating the need for gamma radiation or other treatments to disinfect the dressing materials. In addition, controlled generation of ozone and other active species can be used to assist with sterilization.

Electrospinning a wound dressing in place over a wound, however, limits the types of solvents that can be used to only those solvents that are compatible with the skin or other tissue to which the dressing is applied. Examples of such solvents include water, alcohols, and acetone. Likewise, because the types of usable solvents are limited, the types of additives, such as, for example, absorbents, bactericides, and antibiotics, that can be used in conjunction with the polymer are also limited to those that are soluble, or form a stable dispersion in the particular solvent used. Similarly, the types of polymers that can be used are also limited to those that are soluble in a skin- or tissue-compatible solvent. Biocompatible polymer/solvent combinations include, for example, poly(ethylenimine)/ethanol, poly(vinylpyrrolidone)/ethanol, polyethylene oxide/water, and poly(2-hydroxymethacrylate)/ethanol plus acid. While fibers from such a combination are non-reactive in their spun state, exposure of the fibers to fluids, either from a wound or from external sources, can cause a local pH change from a neutral or nearly neutral pH to one that is acidic or alkaline, depending on the composition of the fiber. For example, when poly(ethylenimine) fiber is exposed to fluid, it will participate in proton transfer, resulting in an alkaline pH in the fluid contacting the polymer.

In one embodiment, the dressing also comprises a closed cell foam to protect the treated area against mechanical disturbance and/or to provide thermal insulation.

Embodiments of the present invention comprising an adhesive component can include at least one fiber formed from a mixture of any of a variety of hydrophilic polymers, elastomeric polymers, and polymers having adhesive properties. The fiber-forming material can be optionally blended with any of a number of medically important wound treatments, including analgesics and other pharmaceutical or therapeutic additives. Such polymeric materials suitable for electrospinning into fibers can include, for example, those inert polymeric substances that are absorbable and/or biodegradable, that react well with selected organic or aqueous solvents, or that dry quickly. Essentially any organic- or aqueous-soluble polymer or any dispersions of such polymer with a soluble or insoluble additive suitable for topical therapeutic treatment of a wound can be employed. When used in applications other than medical dressings, other additives can be used. For example, in spill management applications, particles useful for absorbing a particular type of compound can be encapsulated in one of the polymer components. For example, a non-woven fiber assembly that is useful for managing spills of hydrophobic compounds can have a compound that absorbs hydrophobic compounds encapsulated within one of the polymeric components of the assembly.

The dressing of the present invention can include a mixture of nanofibers that are elastomeric and either hydrophilic, or hydrophobic with hydrophilic particles attached. For example, Waterlock® polymer (Grain Processing Corp., Muscatine, Iowa) can be incorporated into a highly hydrophilic bandage that can hold up to 60 times or more its dry weight in water. Such an elastomeric, water-containing wound dressing material can provide a reservoir of water, and support fluid flow driven by alternating compression and expansion of the bandage. Such a dressing material can also provide transport of therapeutic substances to the wound, and transport of soluble, or water-transportable by-products of healing away from the wound.

It is envisioned that the proportion of each component in the non-woven fiber assembly can vary according to the particular requirements of a specific type of use. It is also envisioned that the proportion of each component in the dressing can vary within the non-woven fiber assembly itself such that the composition of the assembly on one surface differs from the composition of the assembly on another surface. For example, one or more fibers made primarily of an elastomeric polymer can form a surface of the dressing furthest from a wound. The percentage of elastomeric polymer present in fiber in this portion of the dressing can approach and include 100 percent. At the interior of the dressing, one or more fibers having increasing amounts of a hydrophilic polymer can be present. The percentage of hydrophilic polymer present in a fiber at this portion of the dressing can approach and include 100 percent. The thickness of this portion of the dressing can also vary according to the anticipated needs of a particular application. The fiber(s) on the surface of the dressing to be placed in contact with the patient can contain an increasing amount of polymer having adhesive properties. The percentage of adhesive polymer used in fiber in this portion of the dressing will vary with the need for aggressive or non-aggressive adhesion, but can approach and include 100 percent. The transition from one type of polymer to another can be gradual, producing no distinct layers of fiber type within the dressing, or the transition can be abrupt, thereby producing distinct layers within the dressing. The polymer fiber can be applied in a sterile condition. Alternatively, the composition of the at least one fiber can be constant along the length of the fiber.

As described more fully below, the hydrophilic component, when contacted with water, is believed to absorb the water and to expand, thereby surrounding the adhesive component, keeping the adhesive from adhering to the surface of the wound. The hydrophilic component also keeps the dressing moist, facilitates movement of water to the external surface of the dressing, and facilitates the movement of therapeutic substances throughout the dressing. Examples of suitable hydrophilic polymers include, but are not limited to, linear poly(ethylenimine), cellulose acetate and other grafted cellulosics, poly (hydroxyethylmethacrylate), poly(ethyleneoxide), poly vinylpyrrolidone, polyurethanes, polypropyleneoxides and mixtures and copolymers thereof. The hydrophilic component can also be a water absorbing gel such as Waterlock® polymer or carboxymethyl cellulose. The hydrophilic component can be incorporated into the fiber, attached to the surface of the fiber, or physically held between fibers.

The elastomeric component of the present invention provides mechanical strength to the dressing and the ability to conform to stretching skin. Mechanical strength is needed not only to hold the assembly in place during use, but also to facilitate removal of the dressing when it needs to be changed. Examples of suitable elastomeric polymers include, but are not limited to, polyurethanes, polyesters, polyanhydrides, polyamides, polyimides and mixtures and copolymers thereof.

Some embodiments can also include one or more adhesive components for adhering the assembly to a substrate. Suitable polymers having adhesive properties include, but are not limited to, homopolymers and copolymers of acrylates, polyvinylpyrollidones, and silicones and mixtures thereof. The adhesive can be a fiber that forms an open network, attaching the dressing to the wound at many points, but allowing essential passage of fluids through interstices in the adhesive network.

The polymers contained in the fiber can also contribute to more than one to component category. For example, an acrylate-block copolymer can be used. In such a case, the acrylate block contributes adhesive properties while the copolymer block contributes hydrophilic properties.

While not wishing to be bound by any one theory, it is believed that the components of the fiber-forming polymers create structures internal to the fibers by phase separation that are in the form of rods, particles, sheets or other geometrical forms. It is also believed that upon wetting, the hydrophilic component can swell and expand in a way that physically prevents the adhesive component from coming in contact with a substrate surface. Thereby, a medical dressing of the present invention will adhere to undamaged skin, because the hydrophilic polymer has not been contacted by water and has not swollen to surround the adhesive component. The dressing will not adhere to a wound or tissue at an early stage of healing, on the other hand, because moisture from the wound contacts the hydrophilic component causing it to swell and interfere with the adherence of the adhesive to the wound.

In the same way, deliberate wetting of a part of the dressing that would otherwise adhere to the skin will cause the hydrophilic regions to swell. Such wetting and swelling makes the bandage easy to remove. Advantageously, inadvertent wetting should be avoided to keep the bandage in place.

The non-woven fiber assembly can also be used for other applications. For example, the fiber assembly can be used for delivering pesticides, nutrients or other desired compounds to crops. The fiber assembly can adhere to the crops when dry, but can be readily removed by washing with water. The assembly can also be used as a type of sponge or wall-less flask to absorb or contain water or other liquids. The fiber assembly can therefore be useful in diapers, personal hygiene products, absorbent towels and the like.

The present invention also provides a method of making a non-woven fiber assembly, the method comprising the steps of providing at least one fiber-forming material containing an adhesive component, an elastomeric component, and a hydrophilic component, and forming at least one fiber from the fiber-forming material. The fiber assembly of the present invention can be formed from polymers that are soluble in either organic or aqueous solvents. The fiber-forming material can be provided in a solvent such as an alcohol, ethyl acetate, acetone, or tetrahydrofuran (THF), for example. Optionally, the solvent can be biologically compatible.

Methods of the present invention can optionally include a treatment step to provide one or more desired properties to the dressing after formation of the fibers. For example, fiber containing a water-soluble material can be crosslinked to form water-insoluble fibers. In another example, the fiber can be treated to include a therapeutic or pharmaceutical product. Linear polyethylenimine can be treated with nitric oxide to form linear polyethylenimine diazeniumdiolate, for example.

As mentioned above, the relative amounts of the adhesive component, the elastomeric component, and the hydrophilic component can vary over time during fiber formation. Such time-dependant variation can produce non-woven fiber assembly in which the composition at a first surface differs from the composition at a second surface. For example, one or more fibers can be electrospun primarily from an elastomeric polymer to form a surface of a medical dressing that will not contact the patient. As fiber is electrospun to form the interior of the dressing, an increasing amount of a hydrophilic polymer can be used to form the fiber. After a sufficient amount of fiber containing hydrophilic polymer is incorporated into the dressing, an increasing amount of polymer having adhesive properties can be used to form the fiber of the dressing.

The transition from one type of polymer to another can be gradual (i.e. a constant gradient between polymer types), producing no distinct layers of fiber type within the dressing. Alternatively, the transition can be abrupt, thereby producing distinct layers within the dressing. Such abrupt transitions can be accomplished using a stepped concentration gradient from one polymer to another, or a complete transition from one polymer to another in a single step. The transition between regions of the dressing can also be the result of a non-constant or "skewed" gradient between polymer types. Other variations or combinations of transitions can be used in this method. Also, the layers in the center of the dressing can differ from those in other parts of the bandage by controlling the position of the fiber jet with an electric field or air currents, for example.

In one embodiment, a medical dressing is made according to the following method. At least one fiber is electrospun from an elastomeric polymer, such as elastomeric polyurethane, under conditions that produce a fiber containing excess solvent (i.e. a wet fiber), either within the entirety of the fiber or only on the surface of the fiber. The wet fiber or fibers are collected on a receiver such as a non-stick film. The collected wet fiber will fuse at places of intersection at high temperatures, to form a fibrous film with a high water vapor transmission rate and air permeability. The conditions for electrospinning are then changed such that a dry fiber is received over the wet fiber. This can be accomplished, for example, by increasing the distance between the electrospinning device and the receiver. When a layer of dry fiber is laid down on the wet fiber, the composition of the polymer is changed to a hydrophilic polymer, such as a hydrophilic polyurethane. This second polymer can be introduced over a step gradient, a constant gradient, a skewed gradient, or any combination thereof. The concentration of hydrophilic polymer can approach and/or equal 100 percent. A predetermined amount of fiber is deposited and then the composition of the fiber is changed to an adhesive polymer. As with the previous transition between polymer types, the transition can occur via a step gradient, a constant gradient, a skewed gradient or any combination thereof. The composition of this portion of the dressing can approach and/or equal 100 percent adhesive polymer. The adhesive polymer forms the surface of the dressing that is applied to the patient.

In one embodiment, the present invention provides a method for treating a patient comprising applying a medical dressing to a predetermined area of a patient. The dressing contains one or more fibers and contains an adhesive component, an elastomeric component, and a hydrophilic component. This method can be used to apply one or more fibers to a burn, a wound or another area needing protection from contamination or an area requiring treatment with therapeutic or pharmaceutical compounds. The method can include forming the at least one fiber on a separate receiver and then transferring the at least one fiber to the predetermined area of the patient. Alternatively, the method can include applying the at least one fiber directly onto the predetermined area, e.g. by electrospinning the fiber onto the wound.

As suggested above, other additives, either soluble additives or insoluble particulates, can also be included in the liquid(s) to be formed into the at least one fiber. In one embodiment, these additives are medically important topical additives that are provided in at least therapeutically effective amounts for treating a patient. Particular amounts defining effective amounts depend on the type of additive, and the physical characteristics of the wound and patient. Generally, however, such additives can be incorporated in the fiber in amounts ranging from trace amounts (less than 0.1 parts by weight per 100 parts polymer) to 500 parts by weight per 100 parts polymer, or more. Examples of such therapeutic additives include, but are not limited to, antimicrobial additives such as silver-containing antimicrobial agents, and antimicrobial polypeptides, analgesics such as lidocaine, soluble or insoluble antibiotics such as neomycin, thrombogenic compounds, nitric oxide-releasing compounds that promote wound healing such as sydnonimines and diazeniumdiolates, bacteriocidal compounds, fungicidal compounds, anti-viral compounds, bacteriostatic compounds, anti-inflammatory compounds, anti-helminthic compounds, anti-arrhythmic compounds, antidepressants, anti-diabetics, anti-epileptics, antimuscarinics, antimycobacterial compounds, antineoplastic compounds, immunosuppressants, anxiolytic sedatives, astringents, beta-adrenoceptor blocking compounds, corticosteroids, cough suppressants, diagnostic compounds, diuretics, antiparkinsonian compounds, immunological compounds, muscle relaxants, vasodialators, hormones including steroids, parasympathomimetic compounds, radiopharmaceuticals, antihistamines and other antiallergic compounds, anti-inflammatory compounds such as PDE IV inhibitors, neurohormone inhibitors such as NK3 inhibitors, stress protein inhibitors such as p38/NK/CSBP/mHOG1 inhibitors, antipsychotics, xanthines, nucleic acids such as deoxyribonucleic acid, ribonucleic acid, and nucleotide analogs, enzymes and other proteins and growth factors. Additionally, embodiments of the present invention can also include nontherapeutic or inert ingredients such as adhesives, fragrances, and/or odor absorbing compounds.

In still another embodiment, additives that contribute to the structural properties of the article can be included. These include small solid particles, dispersed droplets of immiscible liquids in which other substances can be dissolved, crosslinking compounds, blowing agents to create foams, adhesives, elastomers and the like. Such ingredients can be chosen for their function in protecting and healing the wound.

It will be appreciated that a number of different types of fibrous mats can be produced according to the present invention, depending upon how the fibers are produced and deposited. In one embodiment, the liquid to be formed into fiber is a mixture of an adhesive polymer, a hydrophilic polymer, and an elastomeric polymer. Thus, one fluid provides the entire fibrous mat. However, it is also envisioned that composite fibers of differing compositions can be spun together, or in sequential layers, to provide a suitable fibrous mat.

The method of using a medical dressing of the present invention can comprise applying at least one fiber to a predetermined locus to form a fibrous non-woven matrix. The predetermined locus can be one or more of a wound, an area needing protection from contamination, or an area requiring treatment with therapeutic or pharmaceutical compounds. The dressing can comprise a hydrophilic component, an elastomeric component and an adhesive component.

In another embodiment, a dressing of the present invention additionally comprises at least one pharmaceutical or therapeutic agent selected from antibiotic compounds such as bactericidal and fungicidal compounds, bacteriostatic compounds, crosslinking compounds, analgesic compounds, thrombogenic compounds, nitric oxide releasing compounds such as sydnonimines and diazeniumbiolates that promote wound healing, other pharmaceutical compounds, and nucleic acids, without regard to solubility in a biocompatible solvent. Additionally, this embodiment can contain non-therapeutic or inert ingredients such as adhesives, fragrances, odor-absorbing compounds. In contrast to previous electrospun fibers, the additives are not limited to those that are soluble in the polymer/solvent combination. In some embodiments, insoluble additives are combined with the polymer/solvent combination of the present invention and are incorporated into the fiber essentially unchanged from the form in which they were added.

Finally, the present invention also provides an apparatus for forming at least one composite fiber. The apparatus is capable of forming at least a fiber comprising a hydrophilic component, an elastomeric component and an optional adhesive component. The apparatus comprises a plurality of reservoirs for containing more than one type of fiber-forming material, a plurality of valves each independently in communication with a reservoir, and a fiber-forming device selected from a spinnerette, a NGJ nozzle, and an electrospinning device, in communication with said valves.

An embodiment of one example of an electrospinning apparatus of the present invention can be described with reference to FIG. 1. The apparatus of FIG. 1 comprises a spinning device 10, a fiber-forming device 12, a collection surface 20 and a power supply 30. As can be seen in FIG. 1, spinning device 10 and fiber-forming device 12 are placed at a suitable distance 40 from collecting surface 20.

Figure 9:
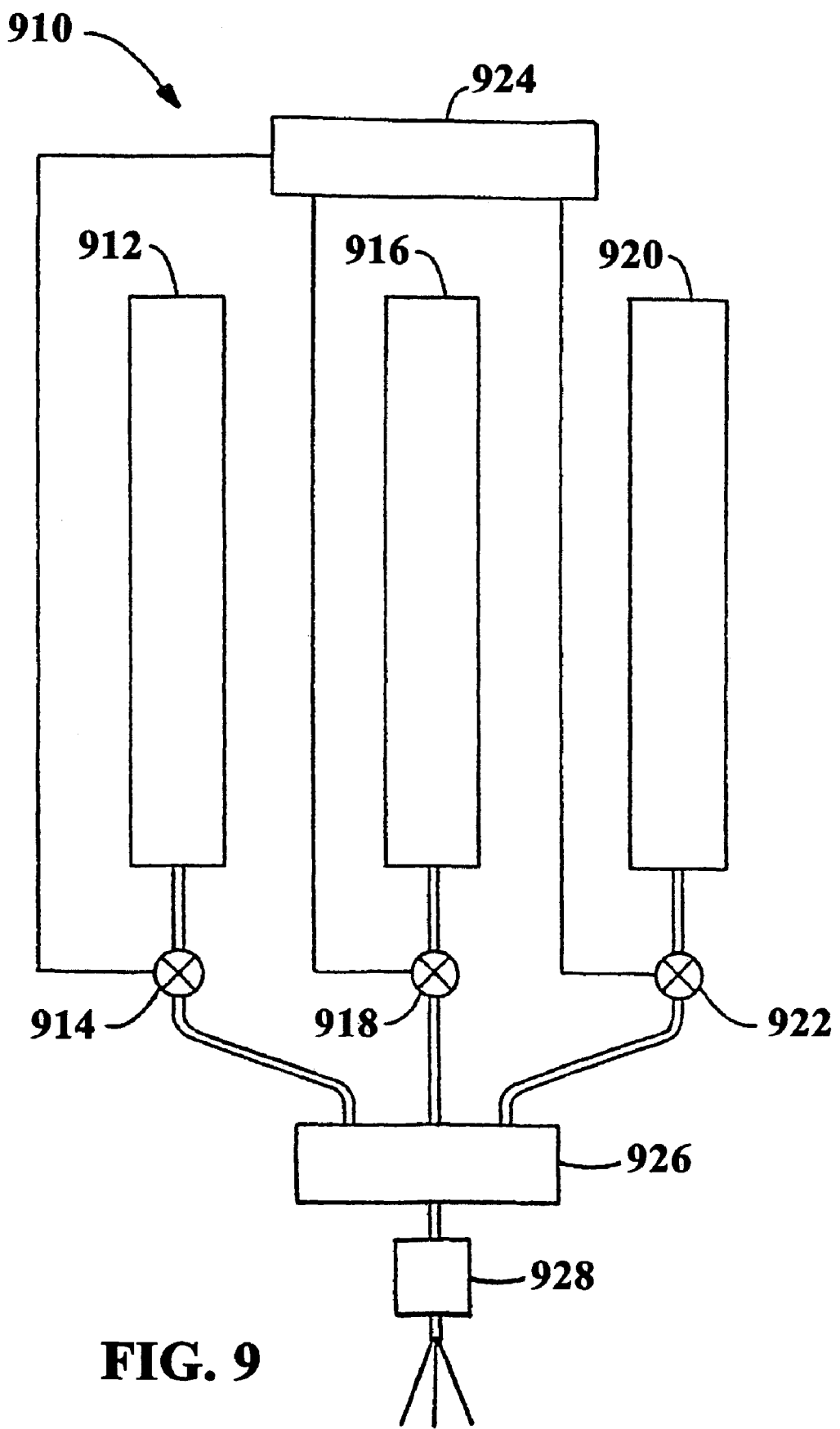
FIG. 9 is a schematic representation of an apparatus for forming composite fibers according to an embodiment of the present invention.
Figure 10:
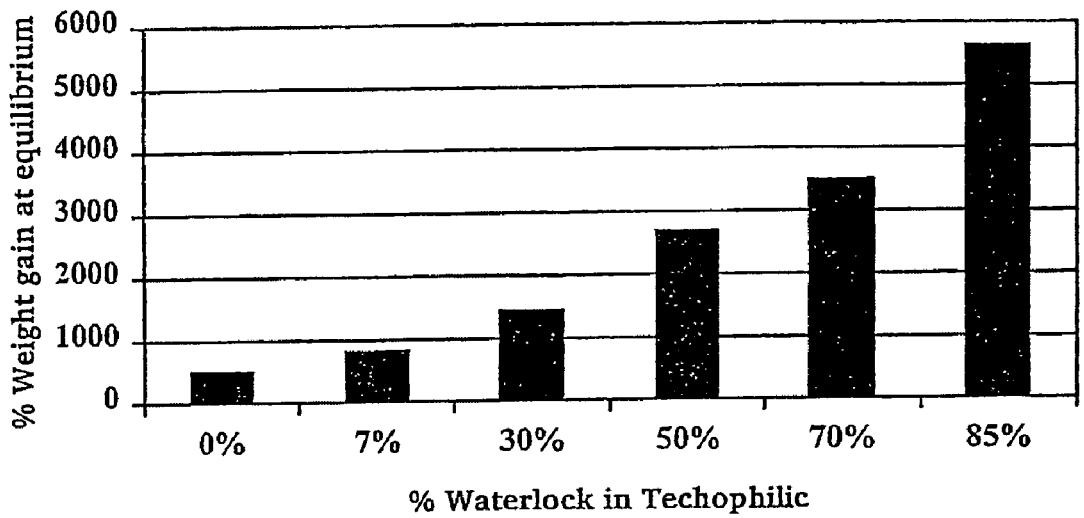
FIG. 10 is a graph showing absorbency of nanofiber assemblies of the present invention.
Figure 11:
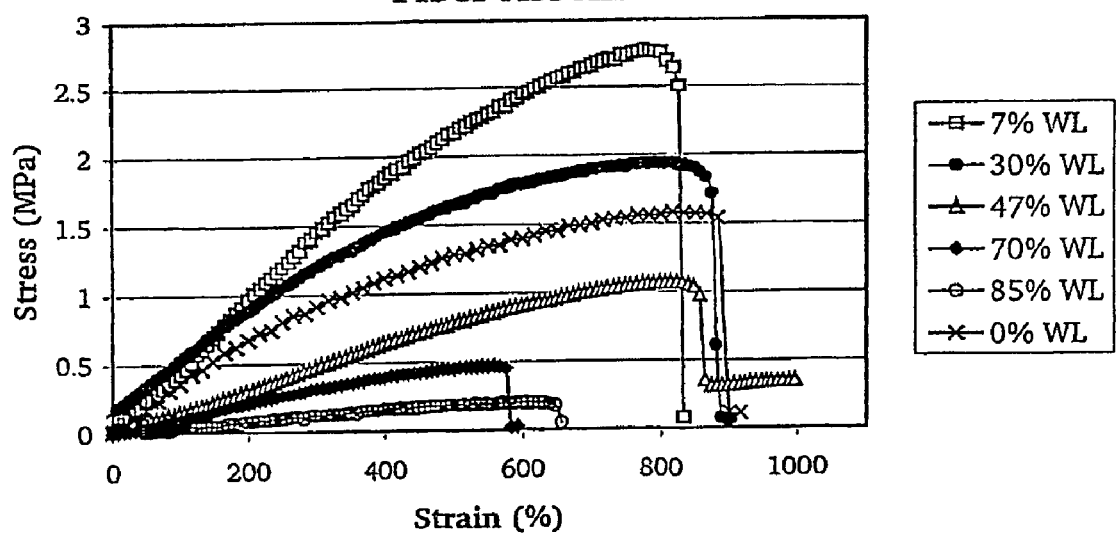
FIG. 11 is a stress-strain curve for nanofiber assemblies of the present invention.

Another apparatus for producing fibers in accordance with one embodiment of the present invention can be described with reference to FIG. 9. Apparatus 910 comprises a first reservoir 912, a second reservoir 916 and a third reservoir 920. First reservoir 912 is in fluid communication with a first valve 914. Likewise, second reservoir 916 is in fluid communication with a second valve 918, and third reservoir 920 is in fluid communication with a third valve 922. First, second, and third valves 914, 918 and 922 can be manually controlled or they can be placed in communication with a controller 924 for automated control. First, second, and third valves 914, 918 and 922 are optionally in communication with a mixing chamber 926, which is, in turn, in communication with a fiber-forming device 928. Alternatively, a fiber-forming device (spinnerette, NGJ nozzle, electrospinning apparatus) can be attached to each reservoir. The rate of fiber production from each device can be regulated to supply the particular polymer in the amount needed to produce the desired spatially variable structure. When the fiber-forming device is an electrospinning device, a power source is in electrical communication with the electrospinning device.

Apparatus 910 can be used to form fibers according to the present invention by placing an elastomeric component, a hydrophilic component, and optionally an adhesive component in each of the reservoirs 912, 916 and 920. The relative amounts of each component fed to fiber forming-device 928 is controlled by selectively opening or closing each of valves 914, 918 and 922. The relative amounts of each component controls the composition of the fibers produced by fiber-forming device 928.

Fibers of the present invention can be fabricated according to a variety of methods known in the art including electrospinning, wet spinning, dry spinning, melt spinning, and gel spinning. Electrospinning is particularly suitable for fabricating fibers of the present invention inasmuch as it tends to produce the thinnest (i.e. finest denier) fibers of any of the foregoing methods. Typically electrospun fibers can be produced having very small diameters, usually on the order of about 1 nanometer to about 3000 nanometers, or from about 10 to about 2000 nanometers, or from about 25 to about 1000 nanometers, or from about 50 to about 500 nanometers, or even about 5 to 100 nanometers. Here as elsewhere in the specification and claims individual ranges may be combined.

Another particularly effective method for producing nanofibers of the present invention comprises the nanofibers by gas jet method (i.e. NGJ method). This method has been previously described and is known in the art. Briefly, the method comprises using a device having an inner tube and a coaxial outer tube with a sidearm. The inner tube is recessed from the edge of the outer tube thus creating a thin film-forming region. Fluid polymer is fed in through the sidearm and fills the empty space between the inner tube and the outer tube. The polymer melt continues to flow toward the effluent end of the inner tube until it contacts the effluent gas jet. The gas jet impinging on the melt surface creates a thin film of polymer melt, which travels to the effluent end of tube where it is ejected forming a turbulent cloud of nanofibers.

Electrospinning and NGJ techniques permit the processing of polymers from both organic and aqueous solvents. Furthermore, adding particle dispersions and soluble non-fiber forming additives (i.e., spin dope) to the fluid to be spun does not prevent the formation of fibrous mats using electrospinning and NGJ techniques. Therefore, a wide variety of additives can be incorporated into fibers and devices of the present invention. Accordingly, absorptive additives can be included such as sodium polyacrylate or 2-propenamide-co-2-propenoic acid, among others.

EXAMPLES

In order to demonstrate the practice of the present invention the following examples have been prepared. Composite fibers are electrospun from a THF:ethanol solution (30:70) containing Waterlock® A-180 and Tecophilic® polymers to form non-woven fiber assemblies or mats. Waterlock® polymers are corn starch/acrylamide/sodium acrylate copolymers available from Grain Processing Corp. (Muscatine, Iowa). Waterlock® polymers contribute a hydrophilic component to the resulting fiber assembly. Tecophilic® is an aliphatic polyether-based polyurethane available from Thermedics Polymer Products (Wilmington, Mass.), which contributes an elastomeric component and a hydrophilic component to the fiber assembly.

The polymer solutions are spun from a conical metal reservoir, and the gap distance is varied with a laboratory jack. The metal cone is suspended with metal wire connected to a high voltage power supply. The voltage and gap distance are varied to produce the best fibers at the highest rate. Aluminum foil covers the target plate, and a square of polyester netting is placed on top of the aluminum foil upon which to collect the fibers. The diameter of the hole at the tip of the metallic reservoir ranges from about 0.5 mm to about 1.5 mm. A larger hole is chosen for higher viscosity solutions. The polymer solution is somewhat more viscous than water in order to make it amenable to spinning. In some embodiments, the reservoir is conical. However, many shapes work equally well. Similarly, in some embodiments the hole in the tip of the reservoir is circular. However, a wide variety of shapes work equally well.

The stock polymer solution is a 14% (w/w) solution of Tecophilic® polymer in ethanol and THF (80:20). This solution is prepared as follows. The Tecophilic® is initially dissolved in excess THF and then concentrated by evaporation. Ethanol is then added to the solution to provide the desired concentrations. The next step is to suspend the absorbent polymer, either Waterlock® or sodium (poly)acrylate (SPA), in ethanol and add the Tecophilic® solution. The absorbent needs to be resuspended periodically, for instance by inverting or shaking the container a few times. Varying concentrations of Waterlock® in Tecophilic® are used, namely: 0, 7, 30, 47, 71, 85, and 95%, wherein each percentage is calculated weight to weight (w/w). A solution of 50:50 (w/w) SPA/Tecophilic® is prepared as well.

The viscosity of the Waterlock®/Tecophilic® solutions is such that the metal conical reservoir that is used can have a hole with a diameter of about 1 millimeter. All samples are spun at a gap distance of 37 cm and with a voltage of 30 kV at room temperature. The SPA/Tecophilic® solution is spun at a voltage of 30 kV with a 30 cm gap distance using a cone that has a hole with a diameter of approximately 1.5 mm. A 25 to 30 g portion of fiber-forming solution is required to produce a fibrous mat with dimensions of approximately 1 mm×10 cm×10 cm, and with a dry weight of approximately 2 grams. The fibers are then removed from the polyester netting and cut into 1.5 cm squares to be tested for absorbency and tensile strength. The diameters of nanofiber segments varies from about 500 to 1500 nm. The thickness of the non-woven sheet varies also, but in most cases, samples with a thickness of about 1 mm are used.

Mats of fibers containing 7, 30, 50, 70, or 85 percent Waterlock® (WL) are tested for their absorbency of water and urine against the absorbency of a mat containing fibers with no Waterlock®. Synthetic urine is prepared by adding the following to distilled water: 25 g urea, 9 g sodium chloride, 2.5 g sodium phosphate, 3 g ammonium chloride, and 3 g sodium sulfite. Once all are dissolved, additional distilled water is added until the total volume is equal to 1 L.

Figure 5:
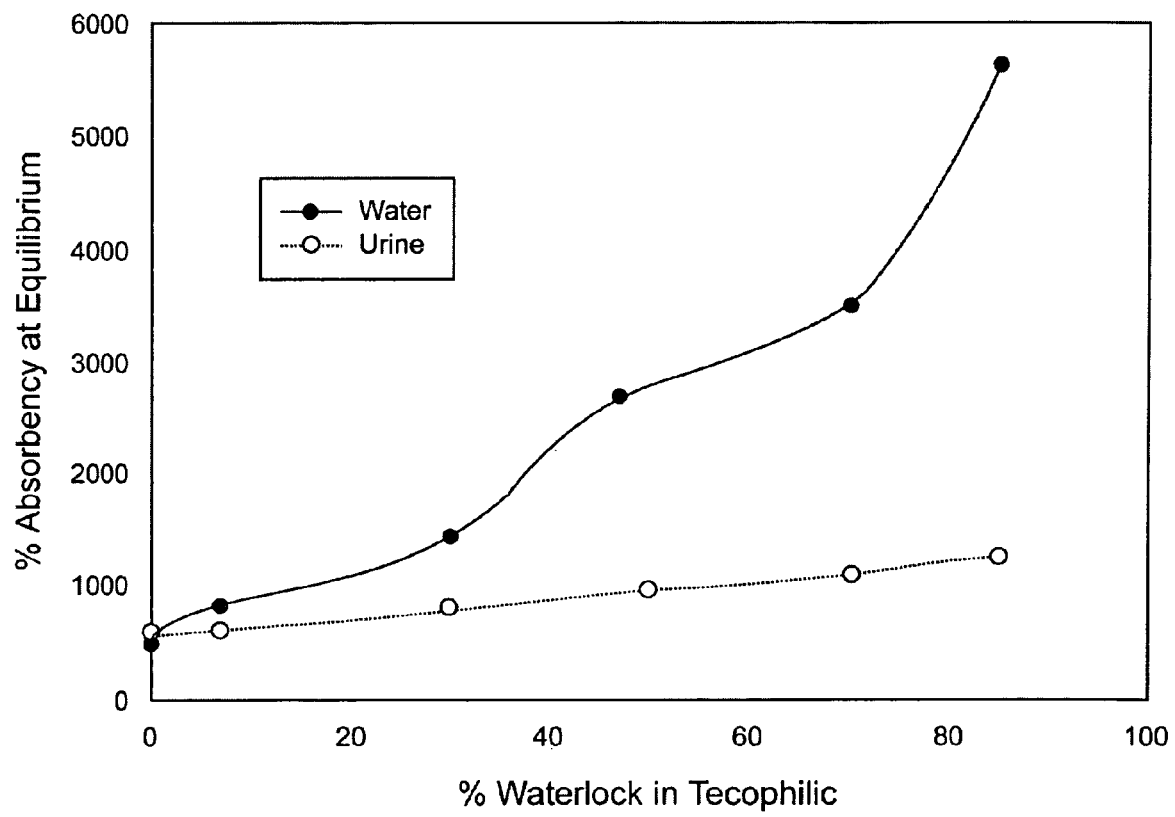
FIG. 5 is a graph of equilibrium absorbency versus percent absorbent where the liquid is either water or urine.

The test procedure is to first weigh the fiber sample and record the dry weight as well as the beginning dimensions. The fiber sample is then placed in a beaker containing either water or synthetic urine and removed after 5 seconds. The wet sample is placed on a paper towel, and the excess water is allowed to drain off. The sample is then weighed and measured. This process continues with weight and size taken after immersion for 0.16, 0.5, 1, 2, 5, and 10 minutes. Finally, the fiber is immersed for at least 24 hours to reach equilibrium absorbency. Absorbency is defined as:

$$Q = (W_2 - W_1)/W_1$$

Where Q is the absorbency, $W_1$ is the initial weight, and $W_2$ is the weight of the fiber mat when wet. The percent absorbency for each sample is shown graphically in FIG. 5. FIG. 5 demonstrates that addition of Waterlock® polymer increases the absorbency of the resulting fiber assembly. Absorbency can also be determined by any of a variety of methods known in the art such as Absorbency Under Load (AUL), or a Gravimetric Absorbency Analysis System (GATS).

Figure 6:
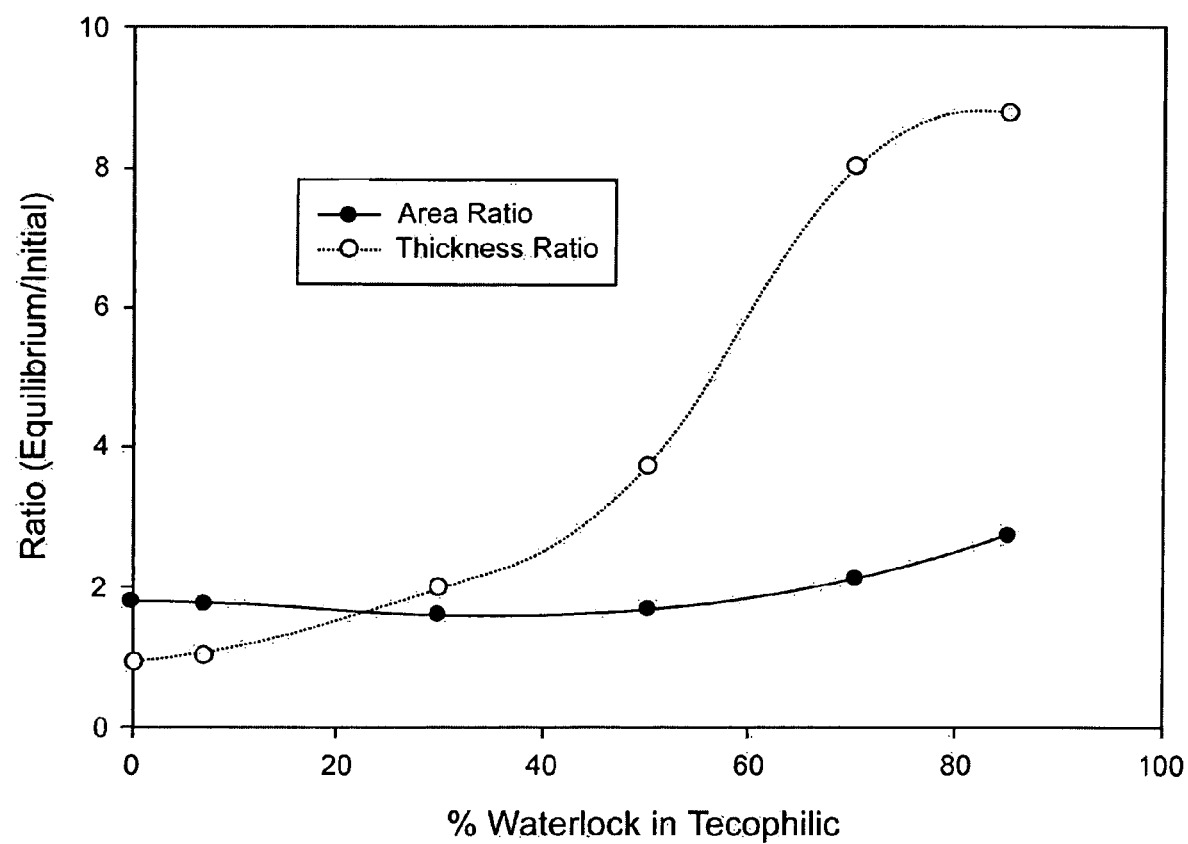
FIG. 6 is a graph of the wet to dry area and thickness ratios versus percent absorbent.

Four samples of each of the Waterlock®/Tecophilic® combinations are tested and the average absorbency of the four samples at equilibrium is calculated. FIG. 6 shows a graph of the ratio of equilibrium over initial absorbency of water by nanofibers that contained 0% to 85% Waterlock® (WL) by weight.

The fiber mats absorbed from 400% to 6000% when placed in water and from 500% to 1250% in synthetic urine. FIG. 5 shows that the nanofibers containing 7% absorbent have very similar results when compared to those nanofibers made up of only Tecophilic® polymer (identified as 0% Waterlock® in Tecophilic® on graph). Also, the increase in absorbency with increasing amounts of absorbent is not as great for the synthetic urine as for the water. FIG. 5 shows the comparison between the absorbency in water and in synthetic urine. As the amount of absorbent increases so does the difference between absorbency in water and in synthetic urine.

The producers of Waterlock® absorbent indicate that it can absorb up to 160 ml of water per gram of polymer. The nanofibers containing HEFC (e.g. Tecophilic®) and absorbent component (e.g. Waterlock®) do not absorb as much water as pure Waterlock® in powder form. The experimental data indicates only 90 ml of water per gram of polymer, a 44% decrease. While not wishing to be bound to any one theory, it is believed that this decrease can be attributed to mechanical restraint of the absorbent component by the HEFC, which limits swelling.

A measure of absorption rate is made by calculating percent absorption at known times. Percent absorption is the ratio of the liquid weight gain at an arbitrary time to the liquid weight gain at equilibrium. Within 5 seconds the 0%, 7%, and 30% Waterlock® samples reaches approximately their maximum absorption. As the amount of Waterlock® increases, the rate at which the fiber absorbed decreases. The 50% and 70% samples absorb greater than 75% of their maximum absorption after 5 seconds. The 85% sample require 2 minutes to reach 73% of its maximum absorption.

The non-woven sheet samples that contained 85% Waterlock® are thicker than the others. Samples from the non-woven sheet used for absorption tests are generally around 1.0 mm thick. Of the four samples of 85% Waterlock® only one is 1.0 mm thick. The other three have thicknesses of 15 mm, 20 mm, and 25 mm. The thicker sheets are observed to take longer times to reach maximum absorption than the thinner sheets. This variation in sheet thickness results in large differences in the observed absorption rates.

The dimensions of each sample are measured when dry as well as when saturated with water. The dimensions are analyzed by calculating the wet to dry ratio of the area and thickness. As the amount of Waterlock® in the samples increases, so does the wet to dry area ratio. The wet to dry thickness ratio does not change significantly with Waterlock® concentration. This indicates that the nanofibers containing no Waterlock® expand most in the length and width dimensions. The addition of an absorbent causes the nanofibers to increase in the length, width, and thickness when wet.

Figure 3:
FIG. 3 is an electron micrograph of a fiber mat before wetting.
Figure 4:
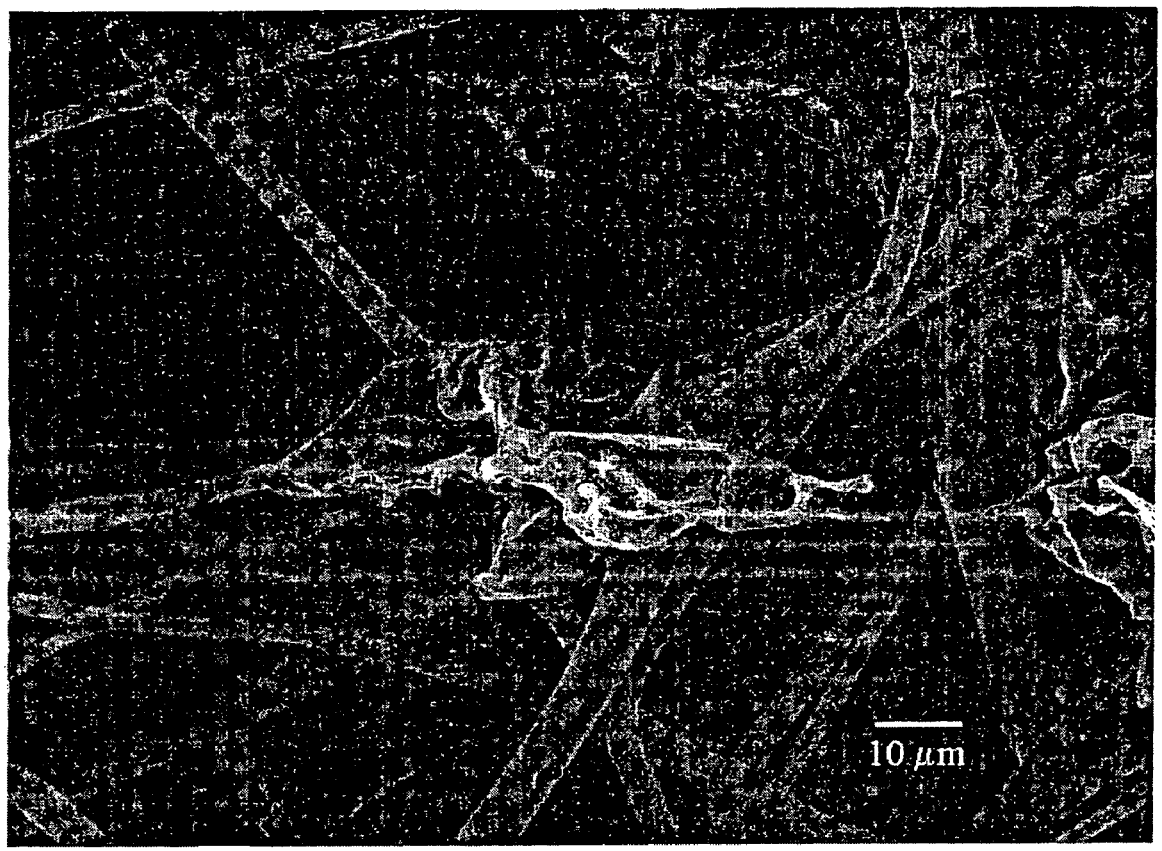
FIG. 4 is an electron micrograph of a fiber mat after wetting and re-drying.

Scanning electron micrographs (SEM's) of fiber mats of the present invention are obtained wherein the mats are in two different states. The first micrograph (shown in FIG. 3) shows the original electrospun fibrous gel, i.e. before wetting. The second micrograph (FIG. 4) shows the fibrous gel after water has been absorbed and then removed by a vacuum. The torn and tangled films of FIG. 4 mark the place of the absorbent particle, which is absent after wetting and drying. It appears that the tangled films held the absorbent particles, which may have been removed by wetting. This result is consistent with the particle being embedded in the HEFC. More particularly, it appears that the particle expanded to the extent that it ruptured the HEFC, leaving behind the empty film within which it was encased. Alternatively, the dry particles of absorbent may have become sheet structures upon wetting, and remained trapped in that morphology after drying.

Figure 2:
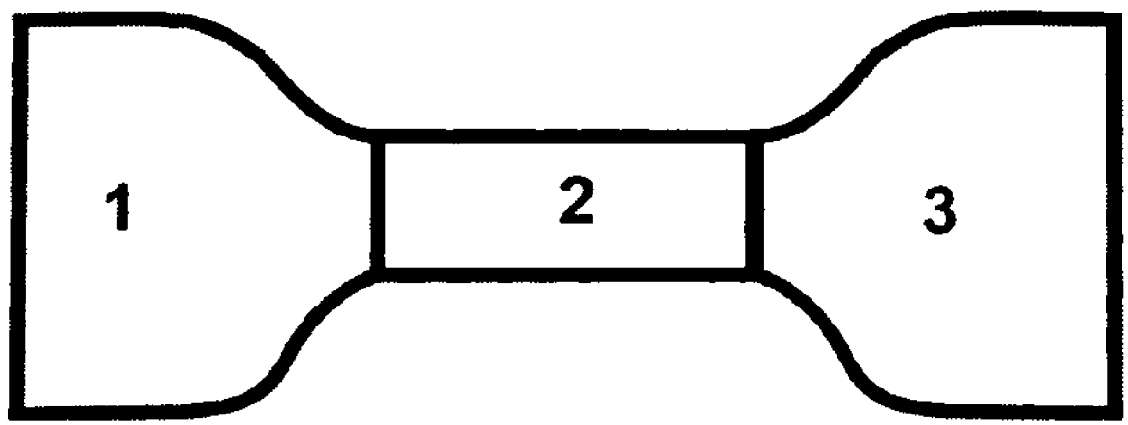
FIG. 2 is a diagram of a tensile test sample.

Ideally, an absorbent is not only capable of absorbing fluids rapidly, but also withstanding mechanical forces while wet. Mechanical tests are performed that measure the amount of stress and strain that the fibrous mat is able to endure before it breaks. An Instron 5567 mechanical testing machine is used. Dumbbells compatible with ASTM 5-D638 are cut from the fibrous mat, shown in FIG. 2. The thickness of the fibrous mat is measured in three places, which are indicated in FIG. 2 by the numbers 1, 2, and 3. Two black lines are placed 10 mm apart to mark the area where elongation is measured. The area between the two black lines is wet with water at least 1 minute prior to conducting the test, since the absorbency tests showed that 95% of total water gain was achieved after 5 seconds. Dumbbell portions 1 and 3 are not wetted and serve as attachments to the grips of the tensile testing machine. The thickness measurements are made at dumbbell portion 2 on the dry sample. Three samples of each of the different concentrations of Waterlock®/Tecophilic® (0, 7, 30, 50, 70, and 85%) are run. All tensile force measurements are made with the grips separating at 50 mm/min.

Figure 7:
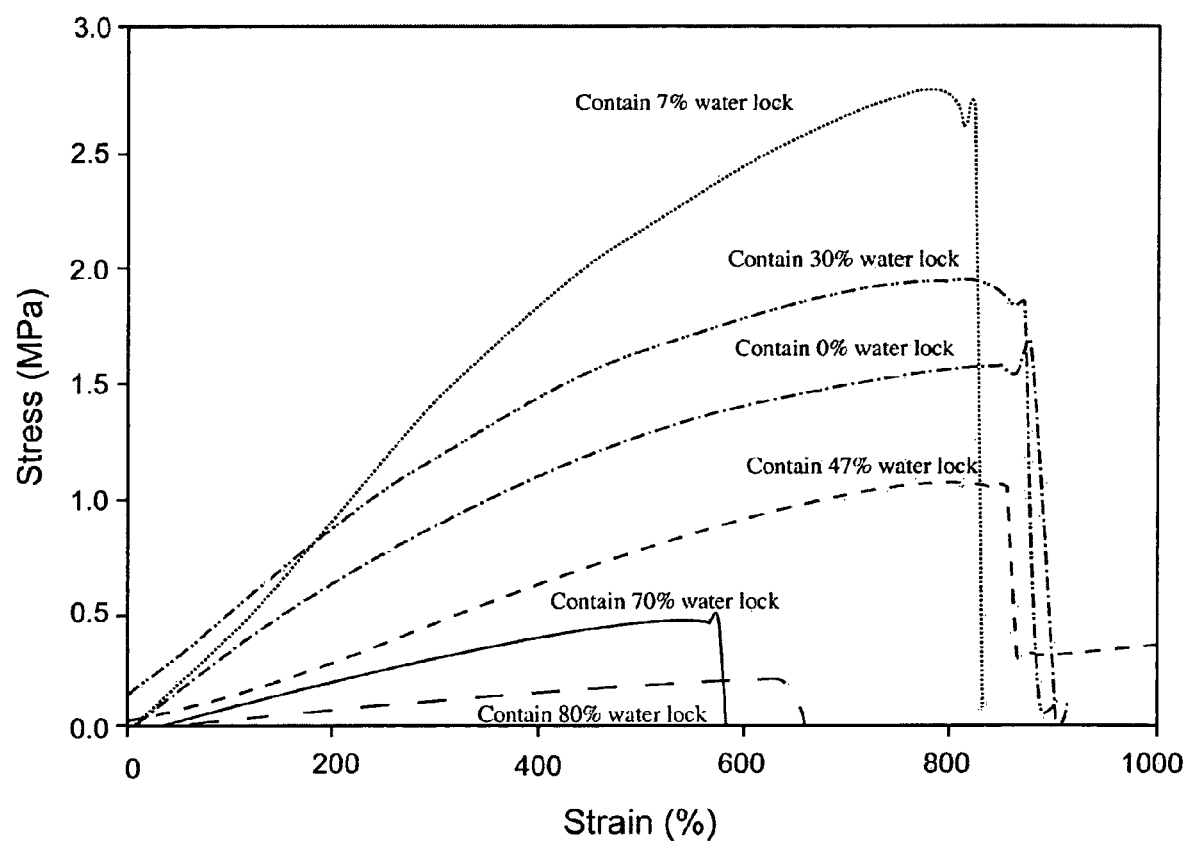
FIG. 7 is a stress versus strain plot for various percentages of absorbent.
Figure 8:
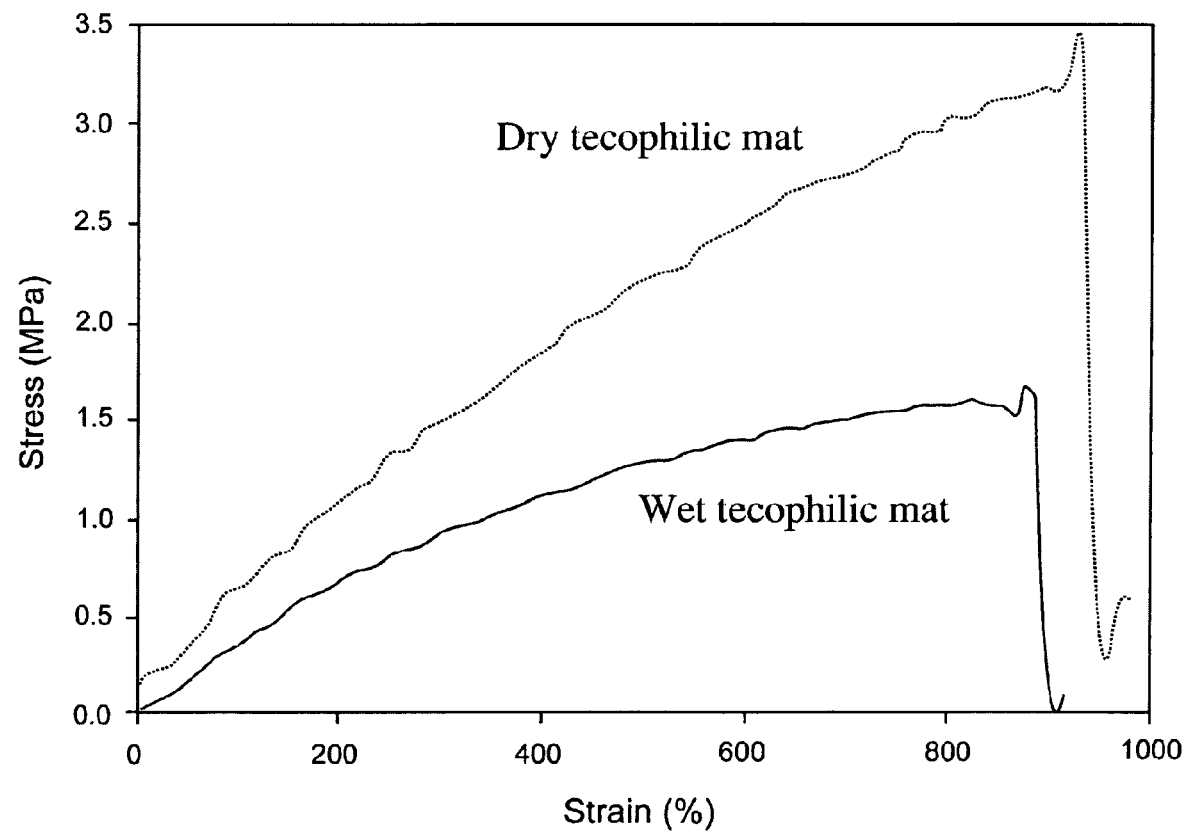
FIG. 8 is a stress versus strain plot for an elastomeric fibrous mat in the wet and dry states.

The samples were stretched at a rate of 50 mm/min The stress-strain behavior of samples containing 7, 30, 50, 70, or 85 percent Waterlock® (WL) is shown in FIG. 7. According to the data, the amount of deformation (i.e. strain) that the samples can absorb exceeds 500% in each case. The tensile strength of the fiber assembly is greatest with seven percent Waterlock®, which was also greater than the Tecophilic® sample (0% WL).

The Tecophilic® polymer provides strength and elasticity for the nanofibers, while Waterlock® does not. The higher the concentration of Waterlock®, the weaker the nanofibers become, as shown in FIG. 7. The nanofibers containing high amounts of Waterlock®, i.e. 70% and 80%, are not mechanically strong, breaking below 0.5 MPa. Those with no Waterlock® at all or only 7% do not break until the stress reaches 2-3 MPa. The 70% and 80% Waterlock® samples also have the lowest strain at their breaking point.

According to these data, the amount of deformation (i.e. strain) that the samples sustain prior to breaking exceeds 500% in all samples. The tensile strength of the fiber assembly is greatest with 7% Waterlock®, which is also greater than that of the sample consisting essentially of Tecophilic® polymer, and being substantially free from Waterlock®. For both the 70 and 80% Waterlock® samples, the break point strain is around 600%. Samples containing lower concentrations of Waterlock® all brake at around 850 to 900%.

The total amount of absorbent material lost from the nanofiber matrix is measured. A sample is taken from the fibrous mat, weighed and then placed in a vessel of known mass. The sample is then immersed in an amount of water for about 24 hours, after which the sample is removed and the remaining solution is evaporated. The mass of the residue left after evaporation is measured and compared to the starting mass of the fiber mat:

$$\% \text{ leachable matter} = \frac{m_{residue}}{m_{i,fibermat}} \times 100$$

The percent leachable matter ranged from about 1.58% to about 4.46%, which is acceptable.

The significance of percent leachable matter stems from the fact that the absorbent is generally embedded in the fibrous component to some degree. If the fibrous material is sufficiently strong it will resist rupture when the absorbent expands due to liquid uptake. Conversely, the fibrous material would be expected to rupture and release the absorbent if it is not sufficiently strong. In practice, it is difficult to completely eliminate rupture; however, formulations exhibiting better strength tend to exhibit less rupture and therefore less leachable matter.

One embodiment of the present invention comprises a bandage that is highly absorbent, and strong even when wet. Another embodiment of the present invention comprises a diaper that is highly absorbent, and strong even when wet. Yet another embodiment of the present invention comprises a highly absorbent and strong device for absorbing spilled liquids. Such liquids include without limitations hazardous chemicals, biohazardous materials, household items, food items, and household or industrial cleaning agents. Still another embodiment of the present invention comprises a device for cleaning such as a mop head, a dishrag, a sanitary wipe, or a floor-waxing device. Still another embodiment of the present invention comprises a toiletry or personal hygiene product including without limitation a sanitary napkin, a tampon, or a sponge for washing.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention pertains.

It is to be understood that any variations evident to one of ordinary skill in the art also fall within the scope of the claimed invention and thus, the selection of specific component elements can be determined without departing from the spirit of the invention herein disclosed and described. Furthermore, the present invention is not to be limited to the examples and embodiments set forth herein, which are only intended to illustrate the present invention. Rather the scope of the present invention is to be determined solely with regard to the claims.

We claim:

1. A liquid entrapping device comprising:
an absorbent component; and
a hydrophilic elastomeric fibrous component,
wherein the absorbent component and the hydrophilic elastomeric fibrous component are in physical proximity thereby resulting in fluid communication,
wherein the absorbent component is more absorbent than the hydrophilic elastomeric fibrous component but wherein the hydrophilic elastomeric fibrous component absorbs more quickly than and has a smaller holding capacity than the absorbent component,
wherein the liquid entrapping device, including the hydrophilic elastomeric fibrous component, is formed from at least one electrospun nanofiber where the at least one electrospun nanofiber comprises both the absorbent component and the hydrophilic elastomeric fibrous component in the nanofiber body, and wherein the absorbent component is embedded in the electrospun hydrophilic elastomeric fibrous component.

2. The liquid entrapping device of claim 1, wherein the absorbent component is selected from polyesters, polyethers, polyester-polyethers, polymers having pendant carboxylic acids or pendant hydroxyls, polysiloxanes, polyacrylamides, kaolins, serpentines, smectites, glauconite, chlorites, vermiculites, attapulgite, sepiolite, allophane and imogolite, sodium polyacrylates, 2-propenamide-co-2-propenoic acid, and any combination thereof.

3. The liquid entrapping device of claim 1, wherein the hydrophilic elastomeric fibrous component is selected from zein protein, polyester elastomers, polydimethylsiloxane, hydrophilic poly(ether-co-ester) elastomers, silicone-co-polyethyleneglycol elastomers, polyacrylates, thermoplastic polyurethanes, poly(ether-co-urethanes), and any combination thereof.

4. The liquid entrapping device of claim 1, wherein the absorbent component is present in an amount from about 1% (w/w) to about 85% (w/w).

5. The liquid entrapping device of claim 1, wherein the absorbent component is present in an amount from about 5% (w/w) to about 50% (w/w).

6. The liquid entrapping device of claim 1, wherein the absorbent component is present in an amount from about 30% (w/w) to about 50% (w/w).

7. The liquid entrapping device of claim 1, wherein the hydrophilic elastomeric fibrous component is selected from polyurethanes, poly ether-co-urethanes, and any combination thereof.

8. The liquid entrapping device of claim 1, wherein the liquid entrapping device comprises a device selected from a diaper, a tampon, a sanitary napkin, a sanitary wipe, a spill absorbing device, a mop head, and a floor waxing device.

9. The liquid entrapping device of claim 1, wherein the liquid entrapping device further comprises an absorbency of water from about 400% to about 6000%, wherein absorbency is defined as $Q=(W_2-W_1)/W_1$.

10. The liquid entrapping device of claim 9, wherein the liquid entrapping device further comprises an absorbency of water from about 500% to about 5500%.

11. The liquid entrapping device of claim 1, wherein the liquid entrapping device further comprises an absorbency of urine from about 500% to about 1250%, wherein absorbency is defined as $Q=(W_2-W_1)/W_1$.

12. The liquid entrapping device of claim 11, wherein the liquid entrapping device further comprises an absorbency of urine from about 500% to about 1000%.

13. The liquid entrapping device of claim 12, wherein the liquid entrapping device further comprises an absorbency of urine from about 600% to about 1000%, wherein absorbency is defined as $Q=(W_2-W_1)/W_1$.

14. The liquid entrapping device of claim 1, wherein the liquid entrapping device further comprises a capacity to absorb about 100% of its equilibrium capacity in about 5 seconds.

15. The liquid entrapping device of claim 14, wherein the liquid entrapping device further comprises a capacity to absorb greater than about 73% of its equilibrium capacity in about 5 seconds.

16. The liquid entrapping device of claim 15, wherein the liquid entrapping device further comprises a capacity to absorb greater than about 75% of its equilibrium capacity in about two minutes.

17. The liquid entrapping device of claim 1, wherein the liquid entrapping device further comprises a tensile strength from about 0 to about 3.0 MPa when the device is wetted with water.

18. The liquid entrapping device of claim 17, wherein the liquid entrapping device further comprises a tensile strength from about 0.25 to about 3.0 MPa when the device is wetted with water.

19. The liquid entrapping device of claim 18, wherein the liquid entrapping device further comprises a tensile strength from about 0 to about 2.8 MPa when the device is wetted with water.

20. The liquid entrapping device of claim 19, wherein the liquid entrapping device further comprises a tensile strength from about 0.25 to about 2.8 MPa when the device is wetted with water.

21. The liquid entrapping device of claim 1, wherein the liquid entrapping device further comprises a breaking point at about 850% to about 900% strain.

22. The liquid entrapping device of claim 1, wherein the liquid entrapping device further comprises a breaking point at about 600% strain.

23. The liquid entrapping device of claim 1, wherein the liquid entrapping device further comprises from about 1% (w/w) to about 5% (w/w) leachable matter.

24. The liquid entrapping device of claim 23, wherein the liquid entrapping device further comprises from about 1.6% (w/w) to about 4.5% (w/w) leachable matter.

25. The liquid entrapping device of claim 23, wherein the liquid entrapping device further comprises from about 1% (w/w) to about 4% (w/w) leachable matter.

26. The liquid entrapping device of claim 1, wherein the absorbent component is a super absorbent.

27. The liquid entrapping device of claim 1, wherein the absorbent component is capable of holding at least about 50 times its own weight in liquid.

28. The liquid entrapping device of claim 1, wherein the nanofibers are electrospun nanofibers having a fiber diameter of about 1 nanometer to about 3,000 nanometers.

29. A non-woven liquid entrapping device comprising:
a super absorbent component; and
a hydrophilic elastomeric fibrous component,
wherein the super absorbent component and the hydrophilic elastomeric fibrous component are in physical proximity thereby resulting in fluid communication,
wherein the super absorbent component is more absorbent than the hydrophilic elastomeric fibrous component, but wherein the hydrophilic elastomeric fibrous component absorbs more quickly than and has a smaller holding capacity than the super absorbent component,
wherein the non-woven liquid entrapping device, including the hydrophilic elastomeric fibrous component, is formed from at least one electrospun nanofiber where the at least one electrospun nanofiber comprises both the absorbent component and the hydrophilic elastomeric fibrous component in the nanofiber body,
wherein the super absorbent component is embedded in the electrospun hydrophilic elastomeric fibrous component, and
wherein the super absorbent component is present in an amount from about 1% (w/w) to about 85% (w/w).

30. The non-woven liquid entrapping device of claim 29, wherein the hydrophilic elastomeric fibrous component is selected from zein protein, polyester elastomers, polydimethylsiloxane, hydrophilic poly(ether-co-ester) elastomers, silicone-co-polyethyleneglycol elastomers, polyacrylates, thermoplastic polyurethanes, poly(ether-co-urethanes), and any combination thereof.

31. The non-woven liquid entrapping device of claim 29, wherein the absorbent component is present in an amount from about 5% (w/w) to about 50% (w/w).

32. The non-woven liquid entrapping device of claim 29, wherein the absorbent component is present in an amount from about 30% (w/w) to about 50% (w/w).

33. The non-woven liquid entrapping device of claim 29, wherein the hydrophilic elastomeric fibrous component is selected from polyurethanes, poly ether-co-urethanes, and any combination thereof.

34. The non-woven liquid entrapping device of claim 29, wherein the liquid entrapping device comprises a device selected from a diaper, a tampon, a sanitary napkin, a sanitary wipe, a spill absorbing device, a mop head, and a floor waxing device.

35. The non-woven liquid entrapping device of claim 29, wherein the nanofibers are electrospun nanofibers having a fiber diameter of about 1 nanometer to about 3,000 nanometers.

36. The non-woven liquid entrapping device of claim 29, wherein the nanofibers are electrospun nanofibers having a fiber diameter of about 10 nanometers to about 2,000 nanometers.

37. A non-woven liquid entrapping device comprising: an absorbent component; and
   a hydrophilic elastomeric fibrous component,
      wherein the absorbent component and the hydrophilic elastomeric fibrous component are in physical proximity thereby resulting in fluid communication,
      wherein the absorbent component is more absorbent than the hydrophilic elastomeric fibrous component, but wherein the hydrophilic elastomeric fibrous component absorbs more quickly than and has a smaller holding capacity than the absorbent component,
      wherein the non-woven liquid entrapping device, including the hydrophilic elastomeric fibrous component, is formed from at least one electrospun nanofiber where the at least one electrospun nanofiber comprises both the absorbent component and the hydrophilic elastomeric fibrous component in the electrospun nanofiber body,
      wherein the absorbent component is embedded in the electrospun hydrophilic elastomeric fibrous component,
      wherein the non-woven liquid entrapping device, including the hydrophilic elastomeric fibrous component, is formed from nanofibers having a fiber diameter of about 1 nanometer to about 3,000 nanometers, and
      wherein the absorbent component is capable of holding at least about 50 times its own weight in liquid.

38. The non-woven liquid entrapping device of claim 37, wherein the hydrophilic elastomeric fibrous component is selected from zein protein, polyester elastomers, polydimethylsiloxane, hydrophilic poly(ether-co-ester) elastomers, silicone-co-polyethyleneglycol elastomers, polyacrylates, thermoplastic polyurethanes, poly(ether-co-urethanes), and any combination thereof.

39. The non-woven liquid entrapping device of claim 37, wherein the absorbent component is present in an amount from about 5% (w/w) to about 50% (w/w).

40. The non-woven liquid entrapping device of claim 37, wherein the absorbent component is present in an amount from about 30% (w/w) to about 50% (w/w).

41. The non-woven liquid entrapping device of claim 37, wherein the hydrophilic elastomeric fibrous component is selected from polyurethanes, poly ether-co-urethanes, and any combination thereof.

42. The non-woven liquid entrapping device of claim 37, wherein the liquid entrapping device comprises a device selected from a diaper, a tampon, a sanitary napkin, a sanitary wipe, a spill absorbing device, a mop head, and a floor waxing device.

43. The non-woven liquid entrapping device of claim 37, wherein the nanofibers are electrospun nanofibers having a fiber diameter of about 10 nanometers to about 2,000 nanometers.

* * * * *